(12) United States Patent
Colladon

(10) Patent No.: US 9,651,522 B2
(45) Date of Patent: May 16, 2017

(54) METHOD OF ANALYZING A PLURALITY OF FERROMAGNETIC PARTICLES

(75) Inventor: Fabrice Colladon, Dammarie-les-Lys (FR)

(73) Assignee: SNECMA, Paris (FR)

( * ) Notice: Subject to any disclaimer, the term of this patent is extended or adjusted under 35 U.S.C. 154(b) by 1004 days.

(21) Appl. No.: 13/639,018

(22) PCT Filed: Apr. 1, 2011

(86) PCT No.: PCT/FR2011/050739
§ 371 (c)(1),
(2), (4) Date: Feb. 5, 2013

(87) PCT Pub. No.: WO2011/121254
PCT Pub. Date: Oct. 6, 2011

(65) Prior Publication Data
US 2013/0130393 A1    May 23, 2013

(30) Foreign Application Priority Data
Apr. 2, 2010  (FR) ..................................... 10 52524

(51) Int. Cl.
*G01N 27/72* (2006.01)
*G01N 1/36* (2006.01)

(52) U.S. Cl.
CPC ............... *G01N 27/72* (2013.01); *G01N 1/36* (2013.01)

(58) Field of Classification Search
CPC ........ G01N 31/22; G01N 33/84; G01N 27/72; G01R 33/1215
See application file for complete search history.

(56) References Cited

U.S. PATENT DOCUMENTS 5,178,692 A * 1/1993 Panchanathan ............... 148/101
6,011,307 A * 1/2000 Jiang et al. .................... 257/746
(Continued)

FOREIGN PATENT DOCUMENTS

JP    58 168939     10/1983
WO   2008 057066    5/2008

OTHER PUBLICATIONS

Coercive Force and Stability of SmCo5 and GdCo5 F.J.A. Den Broeeder and K.H.J. Buschow Journal of the Less-Common Metals, 29, 1972.*

(Continued)

*Primary Examiner* — Krishnan S Menon
*Assistant Examiner* — Dwan A Gerido
(74) *Attorney, Agent, or Firm* — Oblon, McClelland, Maier & Neustadt, L.L.P.

(57) ABSTRACT

The invention relates to a method of analyzing a plurality of ferromagnetic particles (1). The method comprises the following steps:
a) aligning the particles (1) of this plurality in such a manner that each of the particles is oriented substantially in the same direction;
b) fixing the particles (1) of said plurality in the alignment;
c) exposing the internal regions of the particles (1) as aligned in this way;
d) determining the nature of each of the particles and grouping the particles by category as a function of their natures; and
e) in each category, determining the metallurgical structure and the chemical composition of one or more of the particles.

12 Claims, 2 Drawing Sheets

(56) References Cited

U.S. PATENT DOCUMENTS

2005/0173004 A1\* 8/2005 Apostolides ....... F01M 11/0408
137/512
2010/0152052 A1 6/2010 Goodman et al.

OTHER PUBLICATIONS

Fly Ash Characterization by SEM-EDS Barbara G. Kutchko and Ann G. Kim Fuel 85, 2006, 2537-2544.\*
Den Broeder, F.J.A., et al., "Coercive Force and Stability of $SmCo_5$ and $GdCo_5$," Journal of the Less-Common Metals, vol. 29, No. 1, pp. 65-71, (Sep. 1, 1972).
Kutchko, B.G., et al., "Fly ash characterization by SEM-EDS," Fuel, vol. 85, No. 17-18, pp. 2537-2544, (Dec. 1, 2006).
International Search Report Issued Jun. 1, 2011 in PCT/FR11/50739 Filed Jan. 4, 2011.

\* cited by examiner

METHOD OF ANALYZING A PLURALITY OF FERROMAGNETIC PARTICLES

METHOD OF ANALYZING A PLUALITY OF FERROMAGNETIC PARTICLES

The present invention relates to a method of analyzing a plurality of ferromagnetic particles.

A device having a circuit in which a fluid circulates may, in operation, release metallic or other particles into the fluid. By way of example, such a device is an engine, in particular an aeroengine (turbine engine), and the circuit may for example be a cooling circuit or a lubrication circuit. The particles pollute the fluid and need to be removed from the circuit. For this purpose, use is made of magnetic plugs and/or filters that are placed in the circuit in order to trap the particles so that the particles can be removed from the circuit and can be analyzed.

In general, these particles come from various parts making up the engine (or the device), as a result of the parts being worn or damaged. When particles are recovered from a circuit, it is therefore of great importance to identify the parts from which they come so that, where necessary, it is possible to inspect those parts and to replace them, where appropriate.

In order to identify the origins of the particles, it is therefore necessary to analyze each of the particles.

This analysis consists in determining the natures of the particles (metal, ceramic, polymer), and where appropriate their microstructures, in order to identify accurately the parts from which they come. In the vast majority of circumstances, only ferromagnetic particles are of interest, since the parts for which it is desired to determine whether or not they are damaged or worn are ferromagnetic parts.

At present, the particles trapped by magnetic plugs or filters are recovered and then some of the particles are selected randomly and analyzed by an energy dispersive spectrometer (EDS) and by a scanning electron microscope (SEB) in order to determine their chemical composition. Given that the particles have size of millimeter order and that they are recovered in hundreds or even thousands, only a few tens of particles can be analyzed in a reasonable length of time and at reasonable cost.

That method presents the following drawbacks.

The analyzed particles are necessarily selected by chance, since it is not possible to determine metal alloy types from their surface appearance. Most of the time, the particles come from numerous distinct parts and are thus not even analyzed. The presently-used analysis method therefore does not make it possible in exhaustive manner to determine the categories of the metal parts that are worn or damaged.

Examining the surface of a given particle using an SEB and an EDS gives no indication about the metallurgical state of the particle, and in particular about its metallurgical history (previous heat treatment) or its microstructural modifications, and that constitutes a limit.

When the surface of the particle is different from the remainder of the particle (e.g. because the particle is covered in foreign bodies coming from another part as a result of friction, or because the particle is oxidized, or because the particle comes from the surface of the part that was originally subjected to surface treatment), then examining the surface of the particle by means of an SEB and an EDS does not reveal the nature of the remainder of the particle, i.e. its original nature.

These shortcomings in the accuracy of the analysis performed by the presently-used method have already led to aeroengines being dismantled pointlessly and at great expense as a result of the damaged parts not being correctly identified, or have led to engine failures because a defective part was not changed in time.

The invention seeks to propose a method that enables the analysis of ferromagnetic particles recovered by filters or magnetic plugs to be made more reliable.

This object is achieved by the facts of:

a) aligning the particles of said plurality in such a manner that each of said particles is oriented substantially in the same direction;

b) fixing the particles of the plurality in said alignment;

c) exposing the internal regions of the particles as aligned in this way;

d) determining the nature of each of the particles and grouping the particles by category as a function of their natures; and e) in each category, determining the metallurgical structure and the chemical composition of one or more of the particles.

By means of these provisions, the internal region of each particle is laid bare and can subsequently be analyzed directly, thereby solving the difficulties (presence of surface covering or treatment on the particles, surface contamination of the particles by foreign bodies, . . . ) that falsify analyses in prior art methods.

Furthermore, it is possible to count and analyze the categories of metallic particles, and by association to determine accurately the part(s) involved from which some of the particles come.

For example, in step a), the particles are aligned by being put in a magnetic field in a region of the field where the field lines are parallel.

This makes it possible in easy and repetitive manner to align ferromagnetic particles in the same direction, namely the direction of the field lines of the magnetic field B.

The invention can be well understood and its advantages appear better on reading the following detailed description of an embodiment shown by way of non-limiting example. The description refers to the accompanying drawings, in which.

Ferromagnetic particles 1 are collected by filters and/or magnetic plugs and they are brought together so as to form a plurality of particles.

All of the particles 1 of the plurality are aligned in a single step such that each of the particles 1 is oriented substantially in the same direction.

For example, each of the particles 1 extends in a main plane P, and, in step a), the main planes P are all brought substantially into alignment.

The term "main" plane P of a particle 1 is used to designate the plane in which the particle mainly extends, i.e. if the particle were to be placed between two parallel planes that are tangential to the particle, then those two planes would be parallel to the plane P when they are spaced apart by a minimum distance.

Figure 1A:
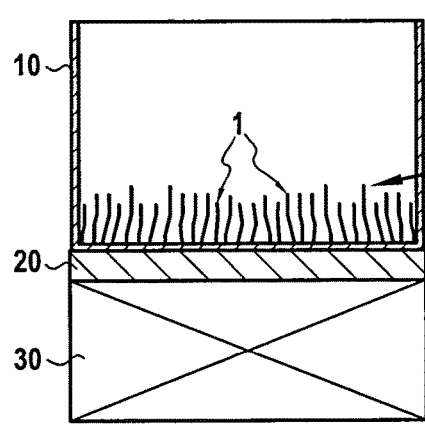
FIG. 1A is a diagrammatic view showing step a) of the method of the invention.

FIG. 1A shows the plane P for a particle 1 of arbitrary shape.

This alignment may be imparted using a magnet, as explained below.

In order to put the particles 1 into alignment (step a) of the method of the invention), the particles 1 are placed on the bottom of a non-magnetic container 10. The container 10 is then placed on a magnet 30. The particles 1 are thus immersed in the magnetic field generated by the magnets 30 and they become distributed while substantially aligning themselves along the field lines L of the magnetic field. At the bottom of the container 10 on which the particles 1 are placed, the field lines L are substantially mutually parallel and perpendicular to the bottom of the container 10, such that the particles 1 are in alignment perpendicularly to the bottom of the container 10.

The particles 1 thus stand perpendicularly on the bottom of the container, as shown in FIG. 1A.

For example, the particles 1 may be aligned in such a manner that one of the main dimensions of each of the particles 1 is substantially perpendicular to the bottom of the container.

Where necessary, a non-magnetic spacer 20 is interposed between the magnet 30 and the container 10 so as to space the container 10 apart from the magnet 30 in such a manner that the field lines L at the bottom of the container 10 are substantially parallel with one another and perpendicular to the bottom of the container 10.

By way of example, the magnet 30 used has a magnetic field with a strength of about 50 amps per meter (A/m).

The method makes it easy to align a large number of particles in a single step.

Thus, the method of the invention is faster and thus less expensive than prior art methods.

Advantageously, the container 10 is transparent, thus making it possible to verify that the particles 1 are indeed in alignment.

The inventors have found that if the container containing the particles 1 is placed in a demagnetizer before placing the particles in the magnetic field of the magnet 20, then, advantageously, the particles 1 tend to move apart from one another, thereby avoiding overlap between them, and facilitating subsequent metallurgical analysis thereof.

Alternatively, it is possible to use means other than magnetic means for spacing the particles 1 apart before aligning them.

The use of a magnetic field for aligning the particles 1 merely constitutes one of the means that enable this alignment to be achieved.

Figure 1B:
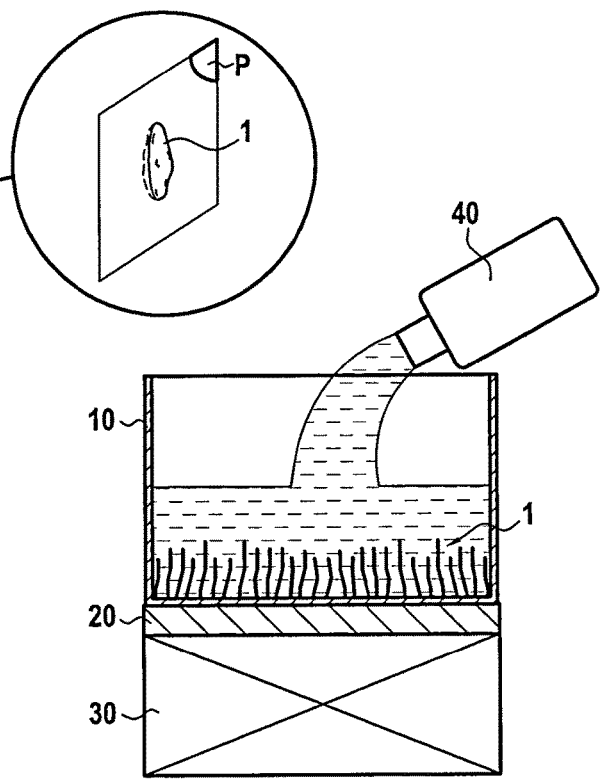
FIG. 1B is a diagrammatic view showing step b) of the method of the invention.

Thereafter, in order to hold the particles 1 in their upright position (in alignment), a material 40 is poured into the container 10 to coat the particles 1 so that they become "potted" therein, as shown in FIG. 1B. The material 40 is sufficiently liquid to coat each of the particles 1 completely without modifying the positions of the particles 1, and it is suitable for solidifying.

By way of example, the material 40 is a resin.

Once the particles 1 are completely coated in the material 40, the material 40 is allowed to solidify, such that at the end of the solidification process the particles 1 are held permanently in the upright position. This step b) of the method of the invention is shown in FIG. 1B.

Throughout the duration of the coating operation and until the resin 40 has completely solidified, the particles 1 are kept immersed in the magnetic field so that the particles 1 are held in the upright position.

Advantageously, a resin 40 is used that is transparent or translucent so as to be able to see the positions of the particles 1.

For example, the resin 40 may be a transparent epoxy resin.

Figure 1C:
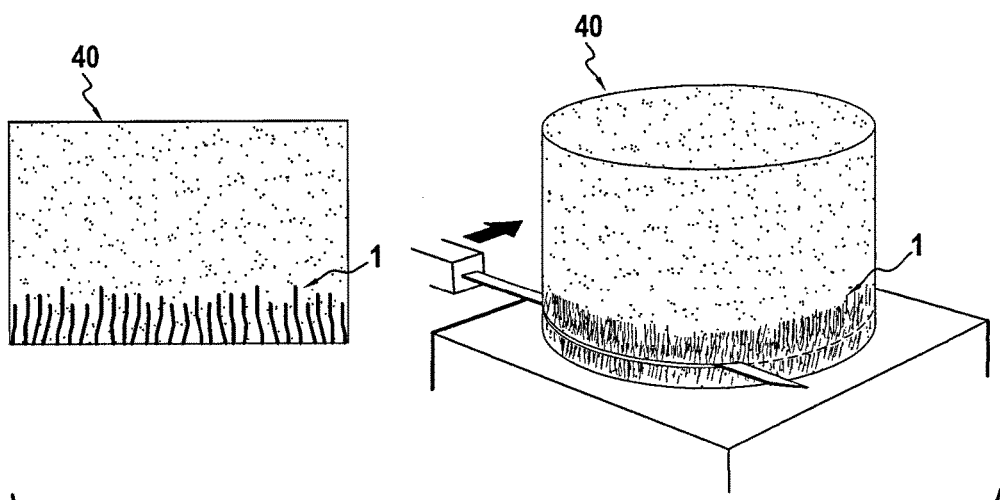
FIG. 1C is a diagrammatic view showing step c) of the method of the invention.

Thereafter, the solidified resin 40 is removed from the container 10. The block of resin 40 is then sliced and polished on a plane that is perpendicular to the alignment direction of the particles 1. This step c) of the method of the invention is shown in FIG. 1C.

Given that the particles 1 are all standing on the bottom of the container 10 when they are coated, the particles 1 are all situated in the same region of the block of resin 40 (the region that was in contact with the bottom of the container 10). By slicing through the block of resin 40 in this region, this positioning of the particles 1 makes it possible in a single step to slice through all of the particles 1, thereby achieving a saving in time.

Furthermore, since all of the particles 1 are aligned perpendicularly to the slicing plane, the cut face 45 (the plane in which the block 40 is sliced, see FIG. 1D), cuts through a central portion of each of the particles 1, thereby exposing their respective inside regions (laying bare their cores). Thus, for each of the particles 1 that is subsequently to be analyzed (steps d) and e)), it is certain that the analysis is well targeted on the material that constitutes the core of that particle (and consequently the material constituting the part from which the particle comes), and not on any covering or surface material on the particle 1.

Furthermore, the resin 40 serves to hold the particles 1 firmly during the cutting process, thereby avoiding any particles 1 coming out of alignment.

Alternatively, the block of resin 40 may be planed until the internal region of each of the particles is exposed.

Thus, in the invention, the internal regions of the particles 1 are all exposed in a single step.

After step c), initial analysis is performed (step d)) that reveals the nature of the alloy constituting each of the particles 1, i.e. the category to which each alloy belongs. In order to determine whether a given particle 1 belongs to a certain category, a test is performed that serves to identify that category, i.e. a test that is representative of that category.

By means of the method of the invention, the internal regions of all of the particles 1 are accessible and visible simultaneously in the cut face 45 of the block of resin 40. Each test that is characteristic of a category thus makes it possible in a single step to reveal all of the particles that belong to that category, thereby saving time. By performing a plurality of tests in succession, where each test is representative of an alloy category, the category to which each of the particles belongs is determined.

For example, the tests may be performed using chemical reagents that serve to reveal the nature of each of the particles 1.

Figure 1D:
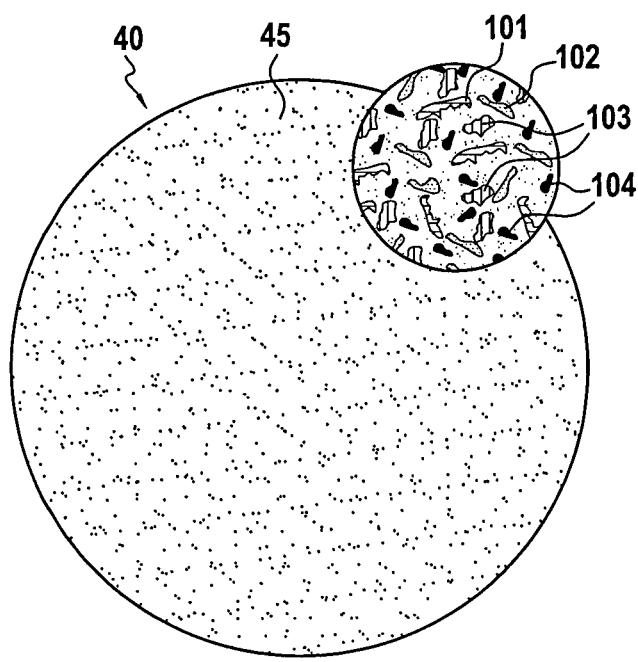
FIG. 1D is a diagrammatic view showing step d) of the method of the invention.

FIG. 1D is a diagram showing an example of the result of tests performed using three known reagents on the cut face 45 of the resin block 40: reagent No. 1 (Nital 2); reagent No. 2 (Nital 6); and reagent No. 3 (15/15). These names are known to the person skilled in the art. Non-alloyed steels react with reagent No. 1 (particles referenced 101 in FIG. 1D), low-alloy steels (reference 102 in FIG. 1D) react with reagent No. 2, and high-alloy steels (particles referenced 103 in FIG. 1D) react with reagent No. 3. The particles that are not etched by any of these reagents (particles referenced 104 in FIG. 1D), are made of other steels or of other alloys.

The reagents are selected in such a manner that each category associated with each reagent covers materials corresponding to a particular category of parts (e.g. the category of bearing steels). It is thus known that all of the particles that react with a given reagent necessarily come from parts of that category.

Advantageously, an optical microscope is used in step d) after the chemical reagents have been applied in order to determine more accurately the nature of each of the particles 1.

In order to identify more accurately the origins of some of the particles, second analysis is performed (step e)) on one or more particles selected from each of the categories identified during the first analysis. Advantageously, there is no need to analyze all of the particles of each category, since, as a result of the first analysis, it is already known that the particles belonging to a given category are substantially identical.

The purpose of this second analysis is to determine the metallurgical structure and the chemical composition of each of the selected particles. This makes it possible to determine accurately the part in the engine (or the mechanical device) from which the analyzed particle comes, with the results of this second analysis being combined with the position of the filter or the magnetic plug from which the analyzed particle was collected, and knowing which parts are present on the path of the fluid circuit that passes through that filter or magnetic plug.

Advantageously, an electron microscope is used together with a spectrometer in order to determine, for each category, the metallurgical structure and the mechanical composition of one or more of the particles 1.

In the prior art method, analysis by means of an EDS is not capable of quantifying the carbon in a metal alloy, so that analysis is not capable of distinguishing between two alloys having carbon contents that are very different but for which the composition of the alloy elements is similar or close. For example, that analysis is not capable of distinguishing between a bolt-grade steel and a bearing steel, and can therefore lead to erroneous conclusions concerning the real origins of the particles.

Figure 1E:
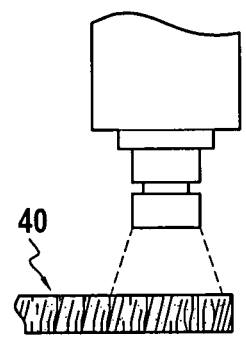
FIG. 1E is a diagrammatic view showing step e) of the method of the invention.

In contrast, in the method of the invention, given that the first analysis (step a)) already provides qualitative information at least in part about the composition of a given particle (e.g. its carbon content), analyses performed using an electron microscope and a spectrometer (FIG. 1E) during the second analysis make it possible to draw reliable conclusions about the chemical composition and the microstructure of that particle.

For example, particles are analyzed using an EDS and an SEB in order to determine their chemical composition and their microstructure.

Figure 2:
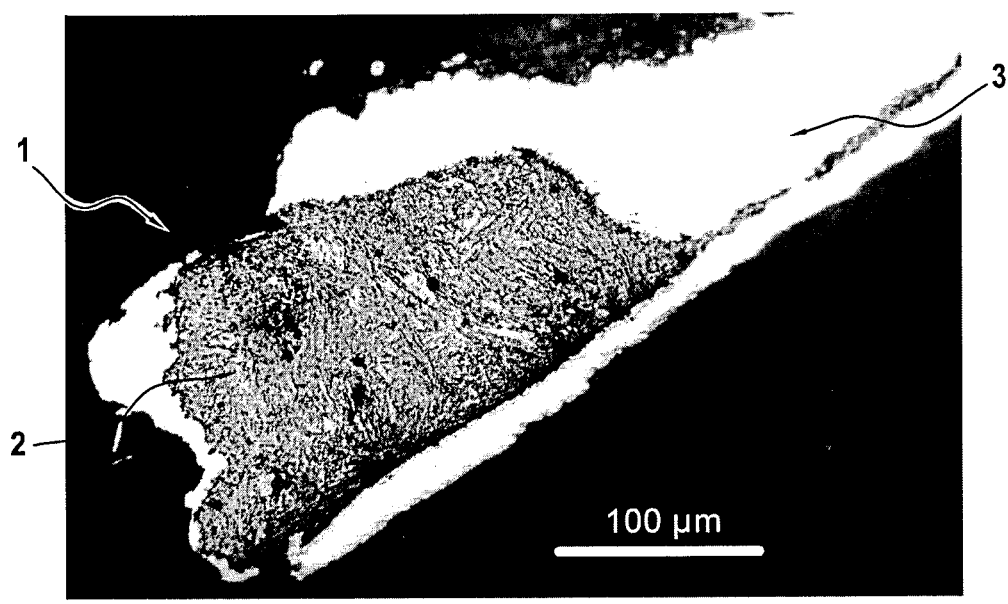
FIG. 2 is a photograph of a particle analyzed by the method of the invention.

FIG. 2 is a photograph of a particle 1 analyzed using the method of the invention, after being examined in step e).

The surface of this particle 1 is covered in a covering 3 of silver. Thus, an analysis of this particle by a prior art method would amount to optically analyzing its surface, and concluding erroneously that the particle is a particle made of silver.

The core 2 of the particle 1 is laid bare by the method of the invention. Analyzing the core 2 with an electron microscope and an EDS reveals that the core is made of a low-alloy steel, having a martensitic microstructure in the tempered quenched state.

It is concluded therefrom that the particle 1 comes from a 40NCD7 steel for a bearing cage. The presence of this particle 1 makes it possible to conclude that there has been damage to a bearing lying on a part of the fluid circuit that passes via the magnetic plug from which the particle 1 was collected. It is therefore necessary to remove and change the bearing.

The invention claimed is:

1. A method. of analyzing a plurality of ferromagnetic particles:
    a) aligning the particles such that each of the particles is oriented substantially in the same direction;
    b) fixing the particles in the alignment, to obtain aligned particles;
    c) cutting the fixed particles in a plane perpendicular to their alignment direction exposing a face of core regions of all of the aligned particles;
    d) treating the exposed faces of the particles with at least one chemical reagent to determine the category of an alloy constituting each of the particles and grouping the particles by alloy category;
    optionally, observing the treated exposed faces in an optical microscope; and
    e) after d), determining the metallurgical structure chemical composition of at least one particle in each alloy category by at least one of electron microscopy and spectroscopy.

2. The method of claim 1, wherein, in a), all of the particles are aligned in a single stage.

3. The method of claim 1, wherein each of the particles extends in a main plane (P), and in a), the main planes are all put substantially into alignment.

4. The method of claim 1, wherein, in a), the particles are aligned by placing them in a magnetic field in a region of the magnetic field where the field lines of the magnetic field are parallel.

5. The method of claim 4, wherein the particles are placed in a non-magnetic container placed above a magnet to place the particles in the magnetic field.

6. The method of claim 5, wherein a non-magnetic spacer is interposed between the magnet and the container.

7. The method of claim 1, further comprising, prior to a):
    placing the particles in a container,
    wherein, in b), the particles are fixed in position by pouring a material into the container, wherein the material coats the particles such that the particles become embedded therein, and on solidifying fixes the particles in an aligned position.

8. The method of claim 1, wherein, in a), the particles are spaced apart before being aligned.

9. The method of claim 8, wherein the particles are spaced apart by placing the particles in a demagnetizer.

10. The method of claim 1, wherein, in d), a chemical etch reagent which reacts with and allows identification of an alloy is applied to the particles.

11. The method of claim 10, wherein, in d), after applying the chemical etch reagent to the particles, the optical microscope is employed to determine the alloy of each category group of particles.

12. The method of claim 1, further comprising:
    collecting the ferromagnetic particles on a magnetic plug or filter in a fluid circuit; and analyzing the collected ferromagnetic particles in a) through e).

* * * * *